(12) United States Patent
Kim et al.

(10) Patent No.: US 12,171,263 B2
(45) Date of Patent: Dec. 24, 2024

(54) AEROSOL GENERATING DEVICE

(71) Applicant: KT&G CORPORATION, Daejeon (KR)

(72) Inventors: Dong Sung Kim, Gyeonggi-do (KR); Heon Jun Jeong, Seoul (KR); Won Kyeong Lee, Seoul (KR); Jae Sung Choi, Gyeonggi-do (KR)

(73) Assignee: KT&G CORPORATION, Daejeon (KR)

( * ) Notice: Subject to any disclaimer, the term of this patent is extended or adjusted under 35 U.S.C. 154(b) by 411 days.

(21) Appl. No.: 17/626,380

(22) PCT Filed: Aug. 9, 2021

(86) PCT No.: PCT/KR2021/010523
§ 371 (c)(1),
(2) Date: Jan. 11, 2022

(87) PCT Pub. No.: WO2022/065679
PCT Pub. Date: Mar. 31, 2022

(65) Prior Publication Data
US 2023/0292839 A1    Sep. 21, 2023

(30) Foreign Application Priority Data

Sep. 24, 2020   (KR) .......................... 10-2020-0123960
Nov. 20, 2020   (KR) .......................... 10-2020-0156917

(51) Int. Cl.
*A24F 40/44*    (2020.01)
*A24F 40/05*    (2020.01)
(Continued)

(52) U.S. Cl.
CPC .............. *A24F 40/44* (2020.01); *A24F 40/05* (2020.01); *A24F 40/10* (2020.01); *A24F 40/20* (2020.01); *A24F 40/30* (2020.01); *A24F 40/485* (2020.01)

(58) Field of Classification Search
CPC .......... A24F 40/44; A24F 40/40; A24F 40/10; A24F 40/20; A24F 40/30; A24F 40/05; A24F 40/485; A61M 15/00
See application file for complete search history.

(56) References Cited

U.S. PATENT DOCUMENTS

| 5,021,701 A | 6/1991 | Takahashi et al. |
| 10,757,971 B2 | 9/2020 | Liu et al. |

(Continued)

FOREIGN PATENT DOCUMENTS

| EP | 3469927 A1 | 4/2019 |
| EP | 3469933 A1 | 4/2019 |

(Continued)

OTHER PUBLICATIONS

Office Action issued Feb. 7, 2023 in Japanese Application No. 2022-508589.

(Continued)

*Primary Examiner* — Jean F Duverne
(74) *Attorney, Agent, or Firm* — Sughrue Mion, PLLC

(57) ABSTRACT

The aerosol generating device includes a storage tank configured to store an aerosol-generating material; a wick configured to absorb the aerosol-generating material stored in the storage tank; a vibrator configured to atomize the aerosol-generating material absorbed in the wick into an aerosol by generating ultrasonic vibrations; a discharge passage configured to discharge the aerosol to an outside of the aerosol generating device; and a structure located at one end of the discharge passage and configured to press the (Continued)

wick toward the vibrator such that contact between the wick and the vibrator is maintained.

12 Claims, 10 Drawing Sheets

(51) Int. Cl.
  *A24F 40/10* (2020.01)
  *A24F 40/20* (2020.01)
  *A24F 40/30* (2020.01)
  *A24F 40/485* (2020.01)

(56) References Cited

U.S. PATENT DOCUMENTS

| | | | |
|---|---|---|---|
| 11,324,253 B2 | 5/2022 | Liu et al. | |
| 2015/0257447 A1* | 9/2015 | Sullivan | A61M 15/06 131/329 |
| 2018/0007968 A1* | 1/2018 | Sur | G01N 27/66 |
| 2019/0223503 A1 | 7/2019 | Liu et al. | |
| 2019/0269177 A1 | 9/2019 | Liu et al. | |
| 2021/0282456 A1 | 9/2021 | Liu et al. | |
| 2021/0378303 A1 | 12/2021 | Liu et al. | |

FOREIGN PATENT DOCUMENTS

| | | | |
|---|---|---|---|
| EP | 3656231 A1 | 5/2020 | |
| EP | 3811804 A1 | 4/2021 | |
| JP | 54-25652 U | 2/1979 | |
| JP | 2-61467 U | 5/1990 | |
| JP | 2019-524120 A | 9/2019 | |
| KR | 10-2019-0034636 A | 4/2019 | |
| KR | 10-2019-0072597 A | 6/2019 | |
| WO | 2016/190577 A1 | 12/2016 | |
| WO | WO-2017139662 A1 * | 8/2017 | ........... A24F 40/485 |
| WO | 2017/206211 A1 | 12/2017 | |
| WO | 2018/024004 A1 | 2/2018 | |
| WO | WO-2019162372 A1 * | 8/2019 | ............. A24F 40/30 |
| WO | 2020/007321 A1 | 1/2020 | |

OTHER PUBLICATIONS

International Search Report for PCT/KR2021/010523 dated Nov. 12, 2021 [PCT/ISA/210].
Written Opinion for PCT/KR2021/010523 dated Nov. 12, 2021 [PCT/ISA/237].
Extended European Search Report dated Jul. 15, 2022 from the European Patent Office in EP Application No. 21834702.9.

* cited by examiner

[Fig. 1]
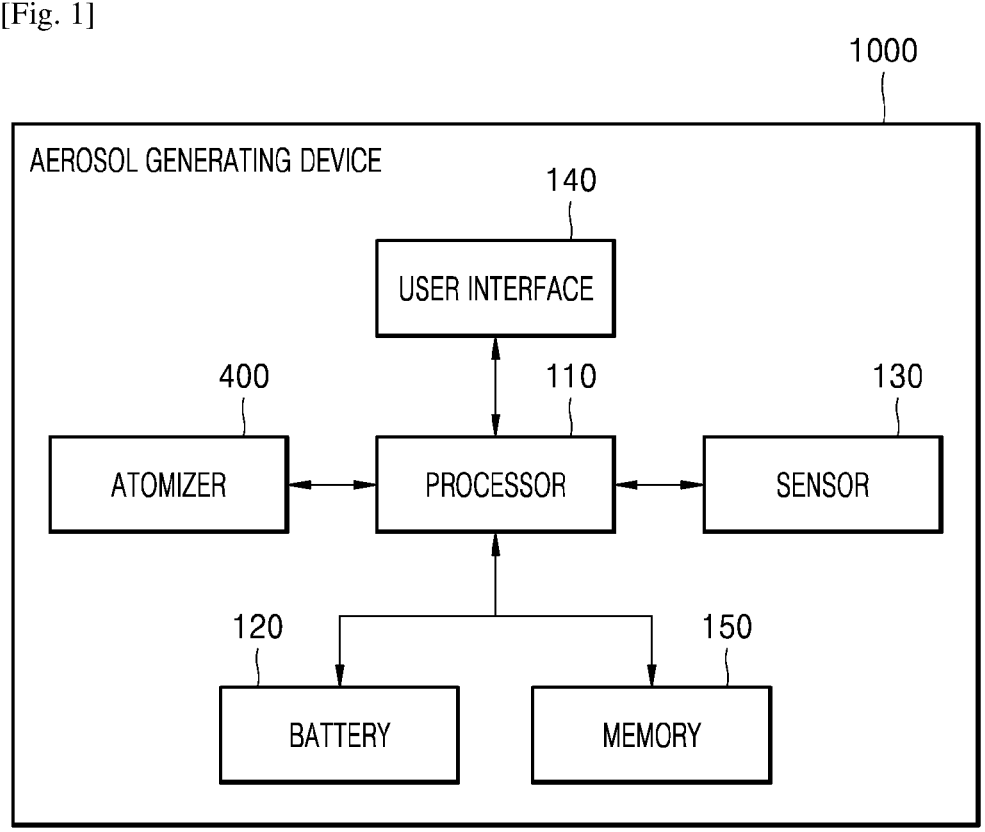

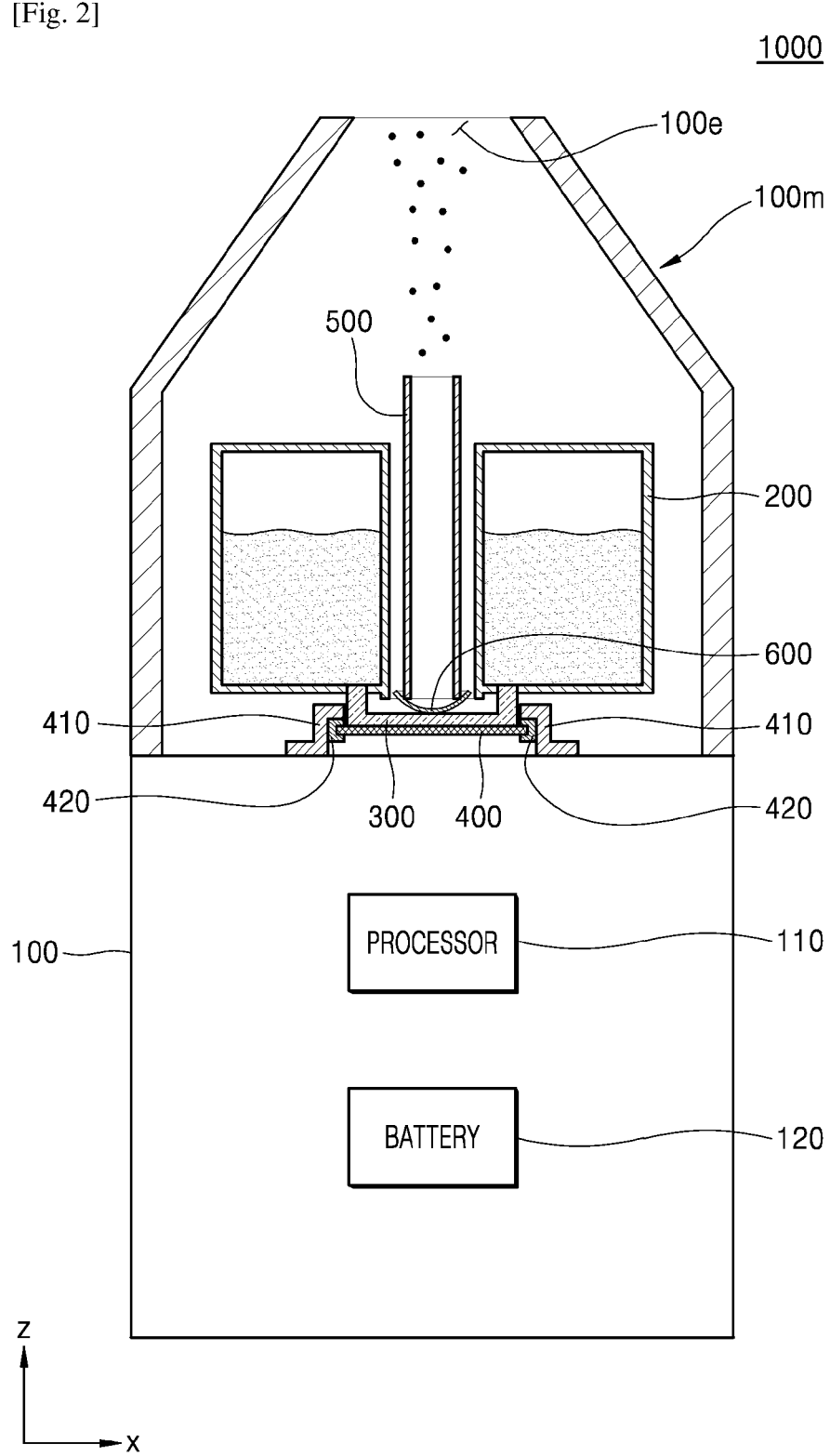
[Fig. 2]

[Fig. 3]
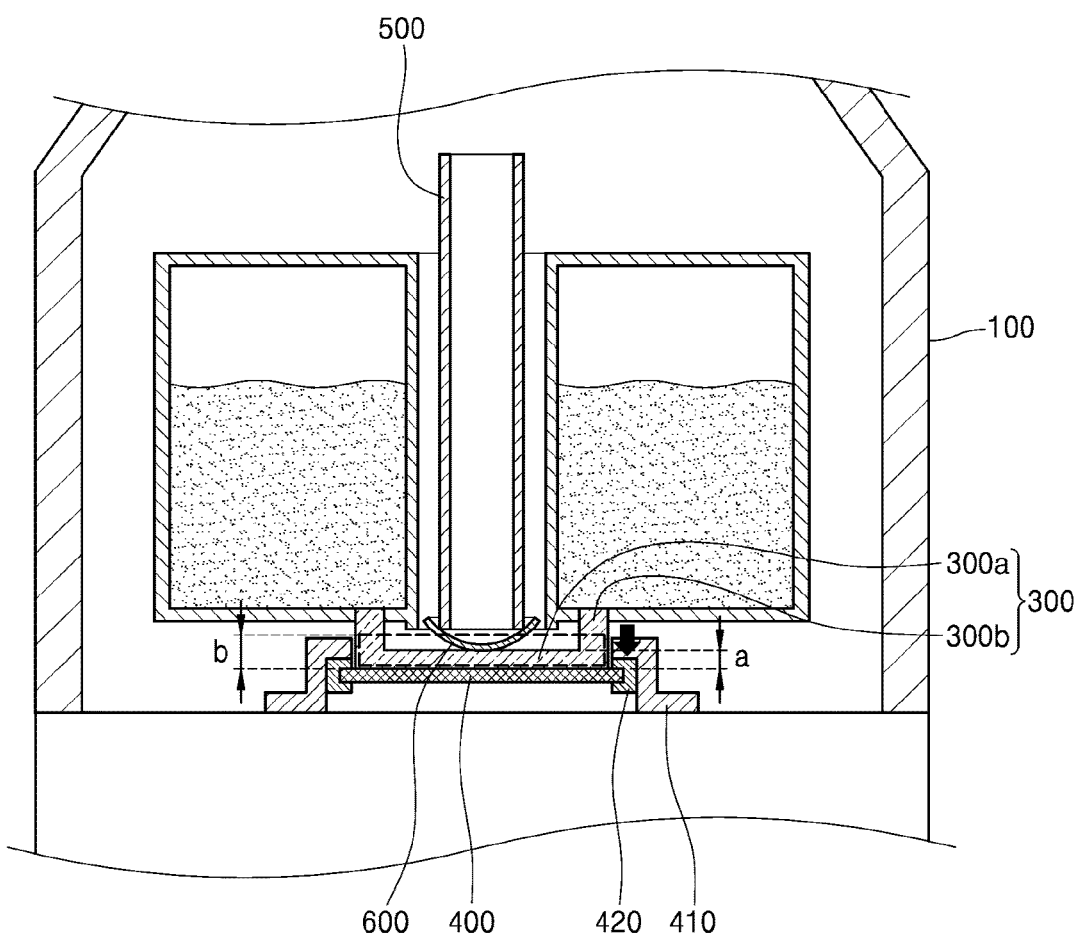
[Fig. 4A]
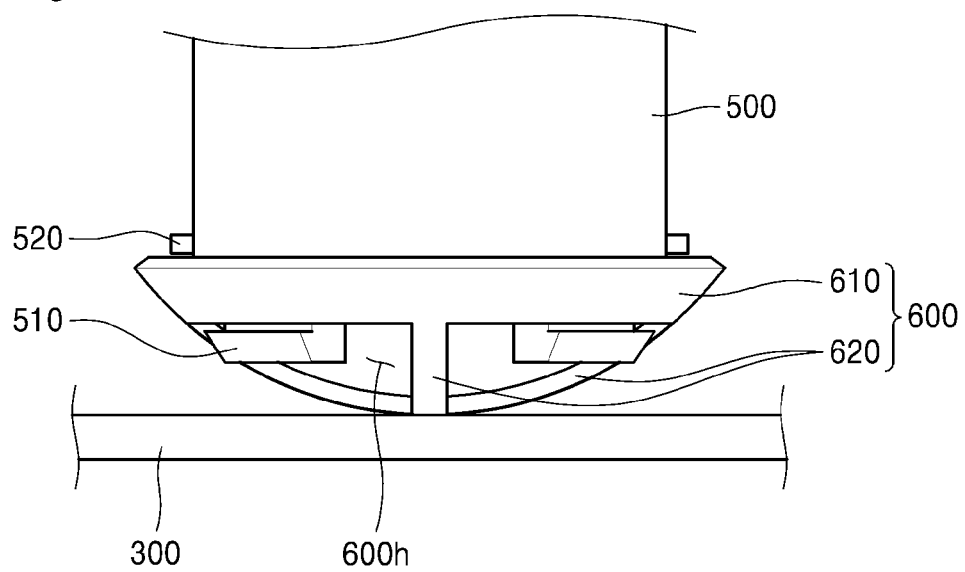

[Fig. 4B]
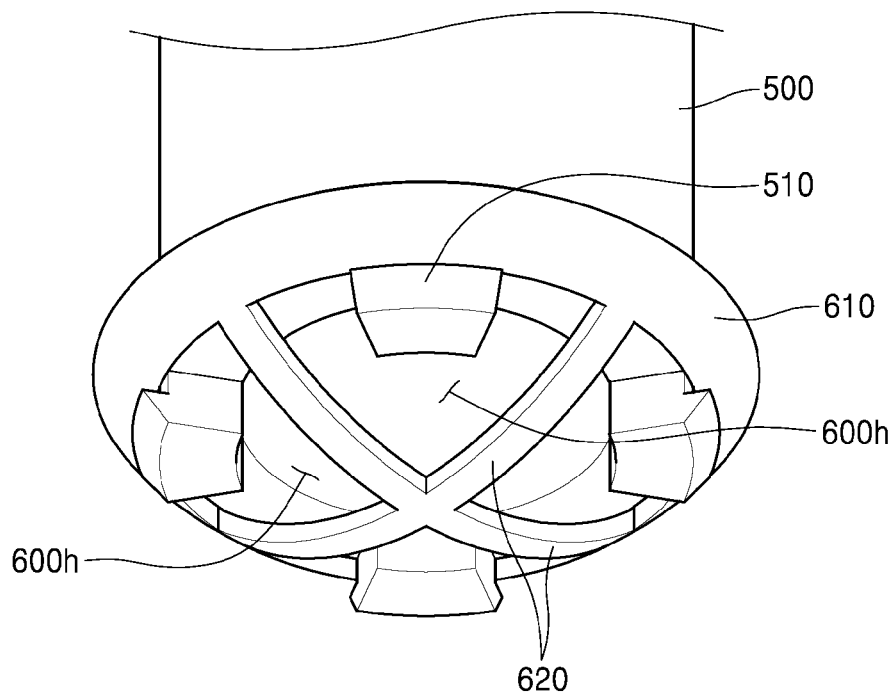
[Fig. 4C]
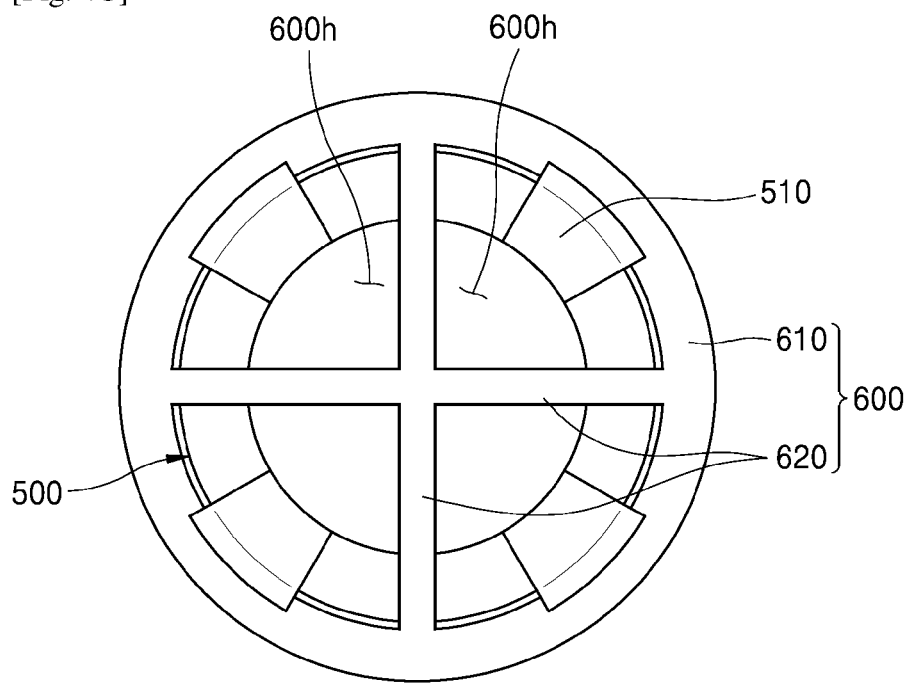

[Fig. 5A]
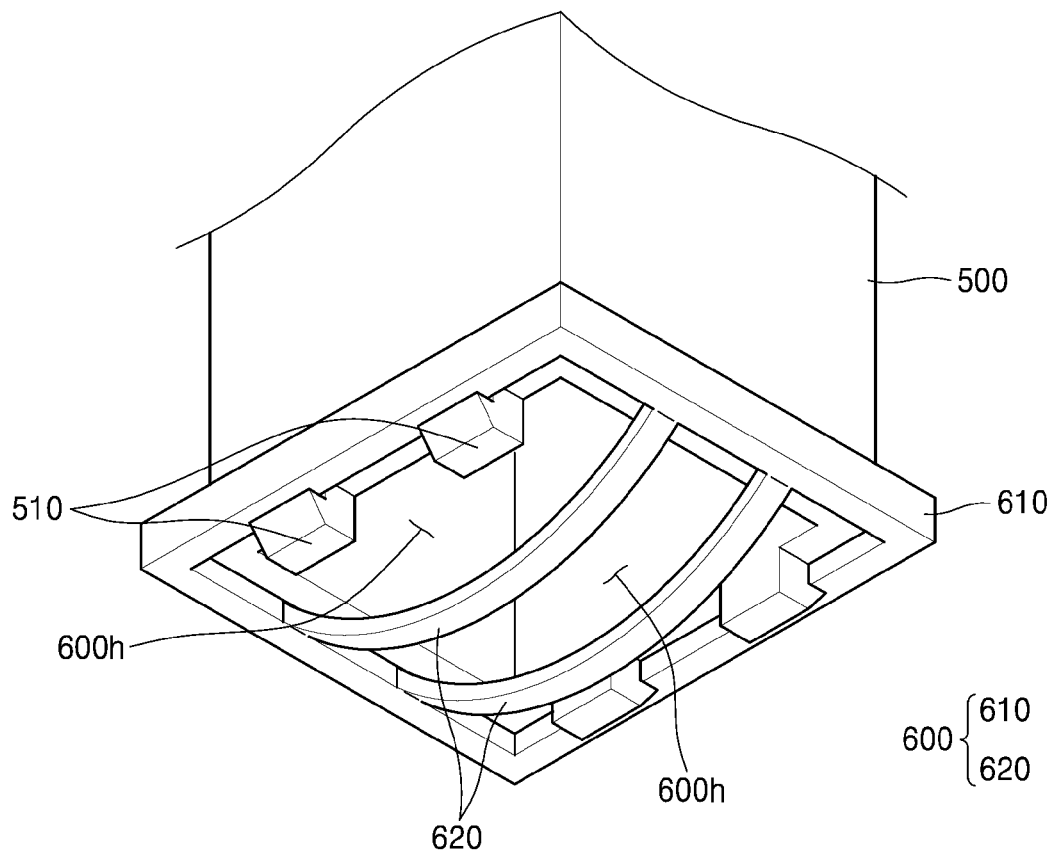
[Fig. 5B]
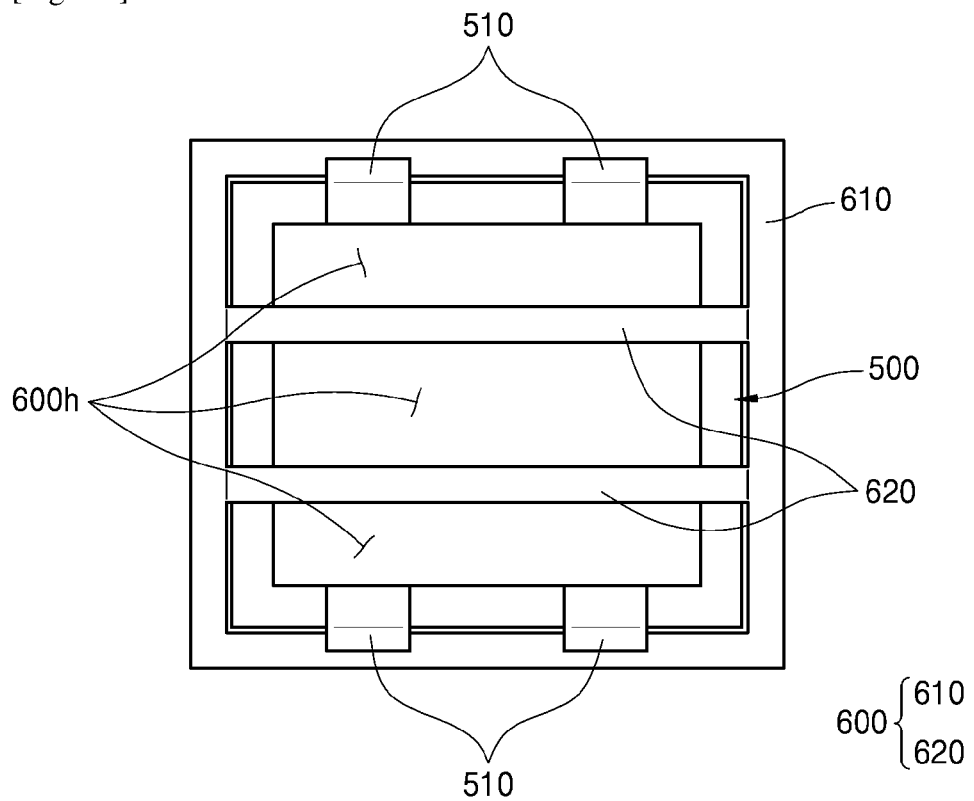

[Fig. 6A]
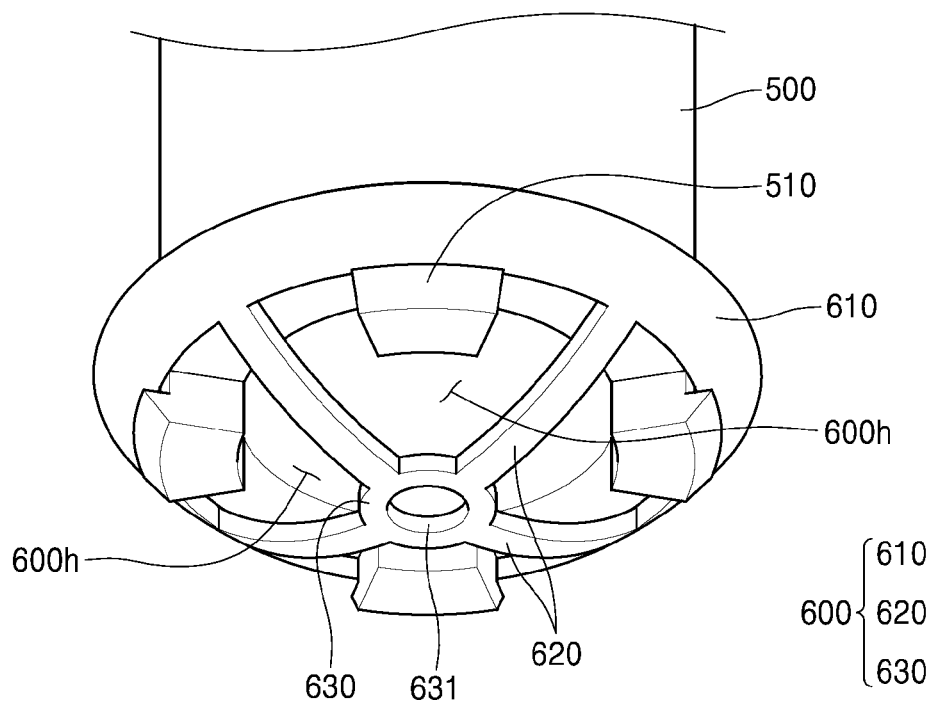
[Fig. 6B]
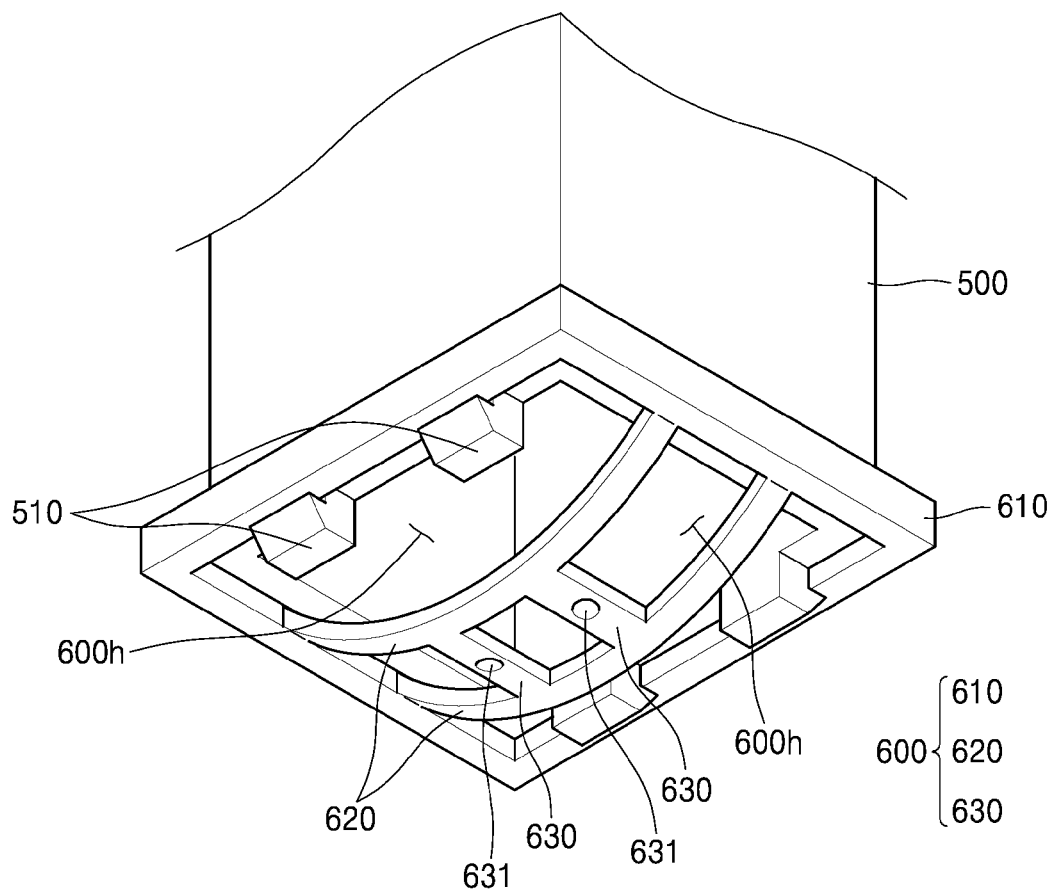

[Fig. 7A]
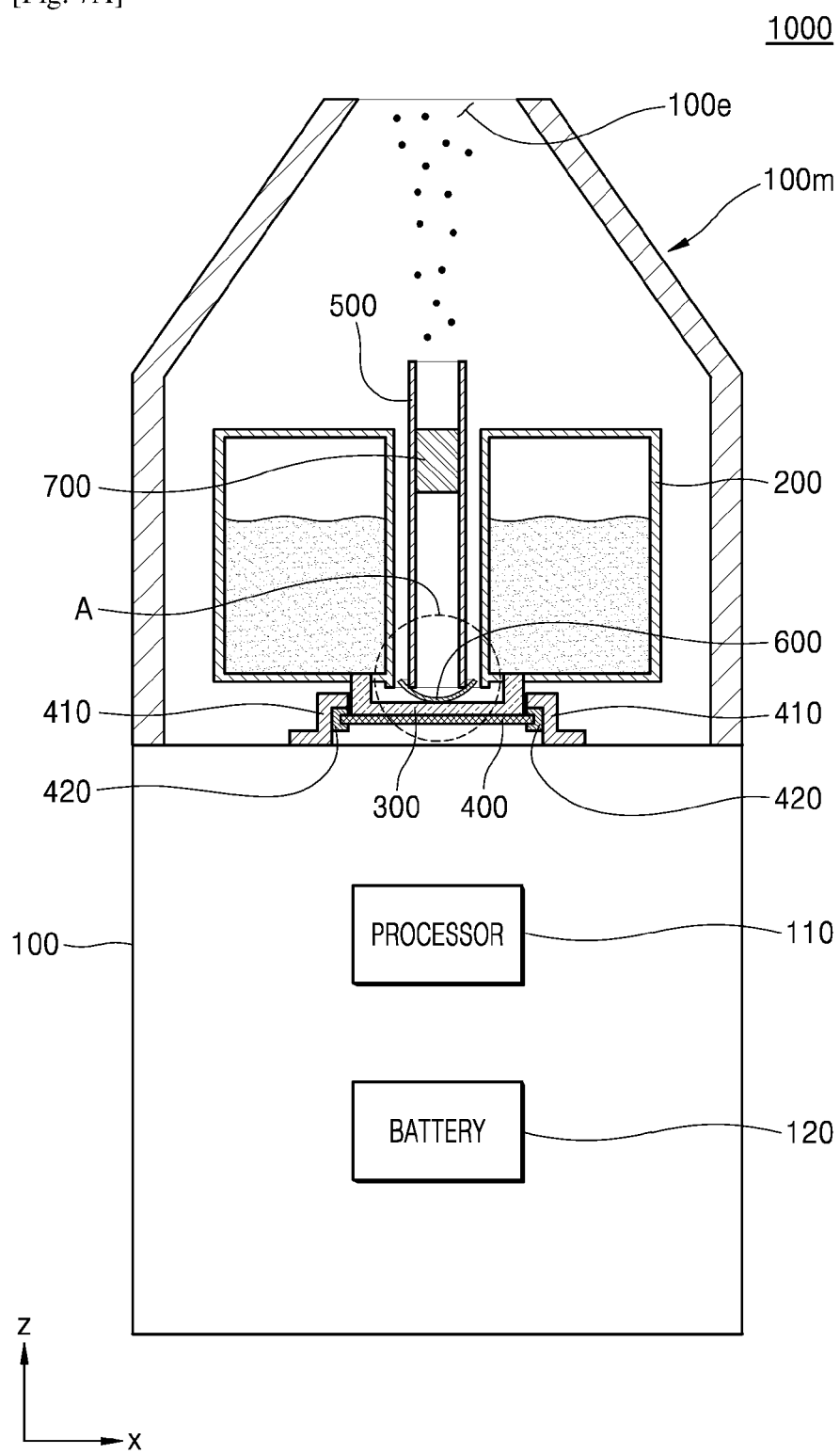

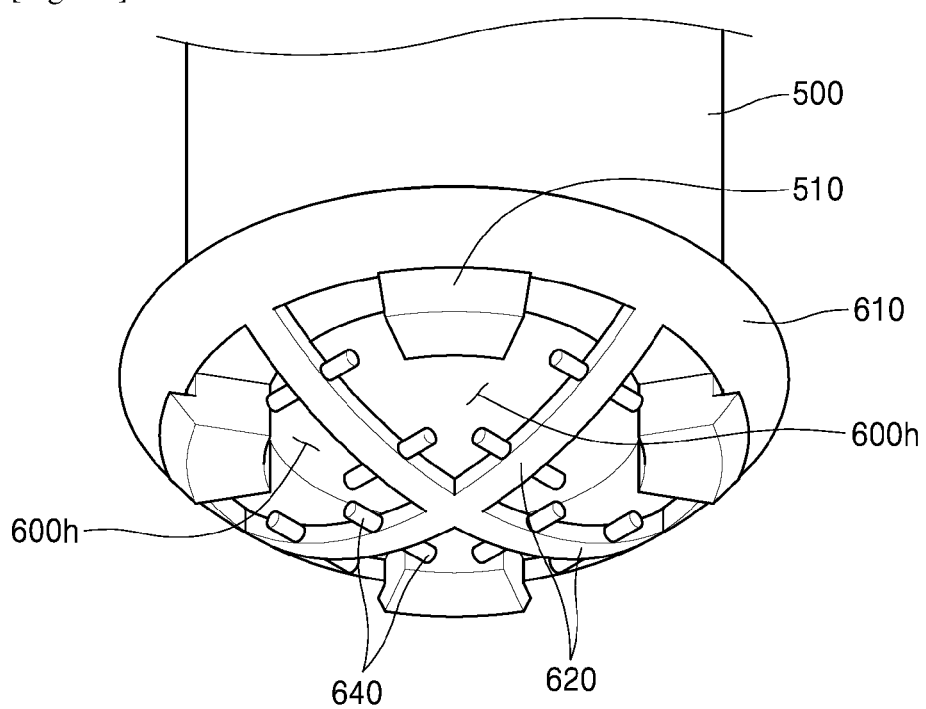
[Fig. 7B]

[Fig. 8]
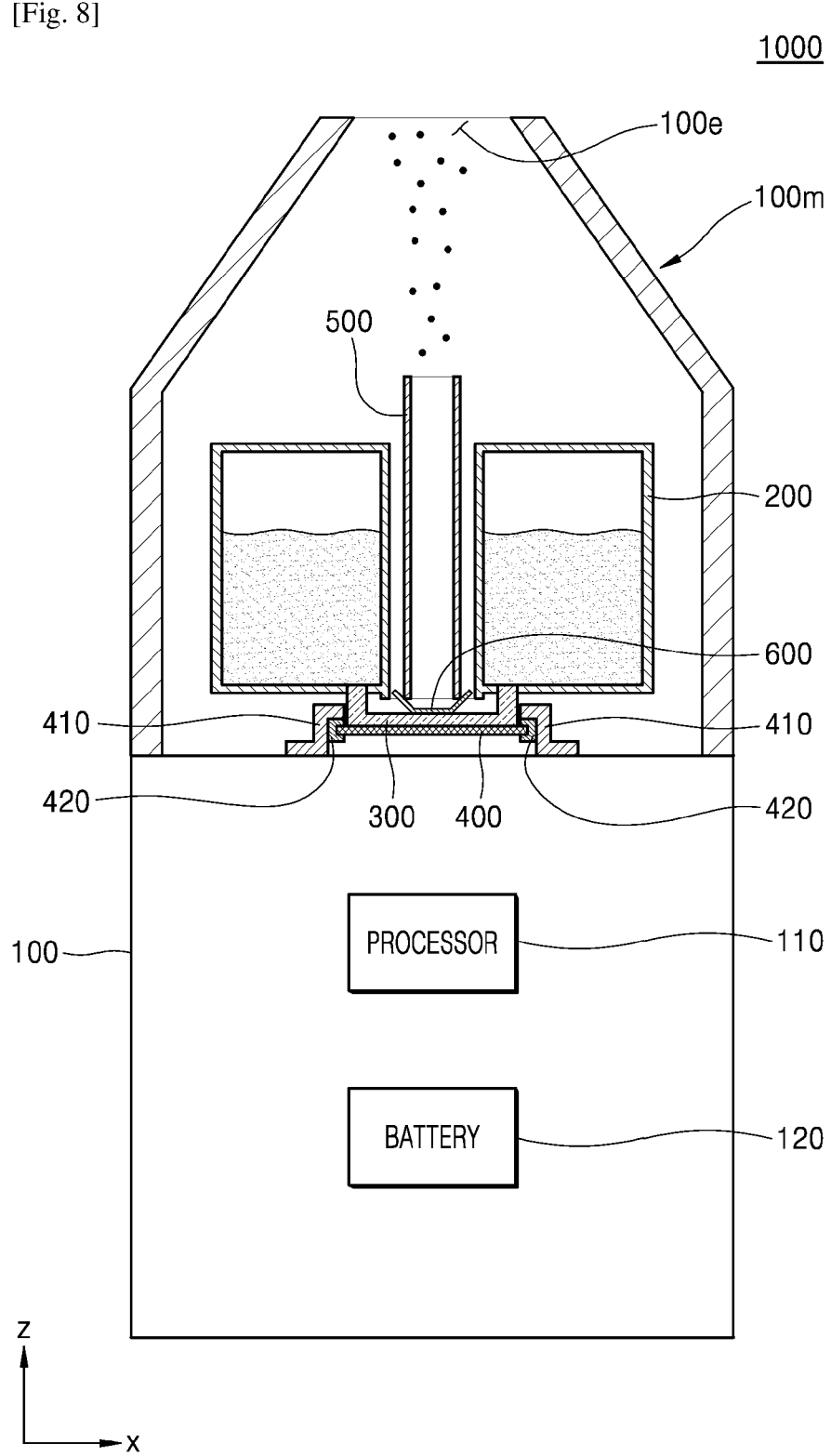

[Fig. 9A]
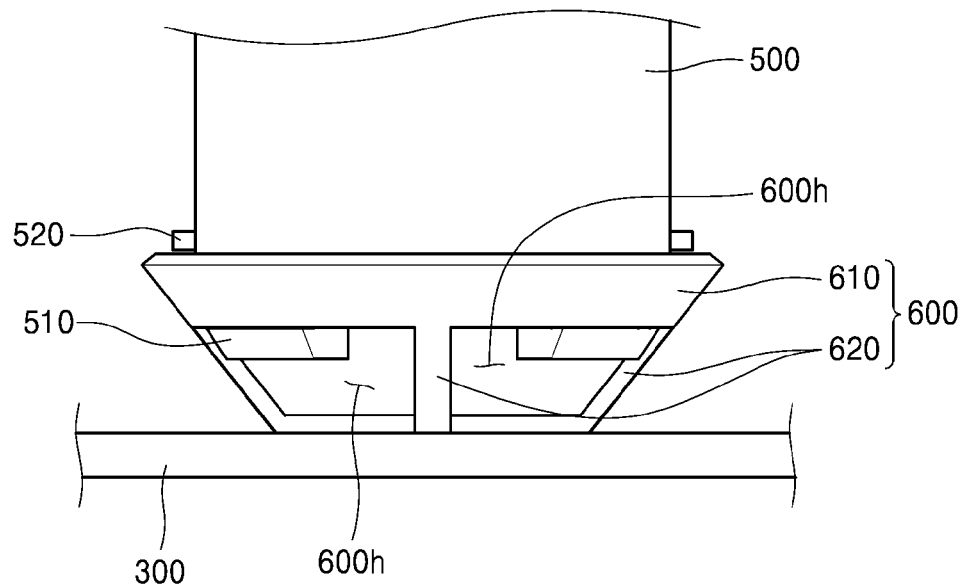
[Fig. 9B]
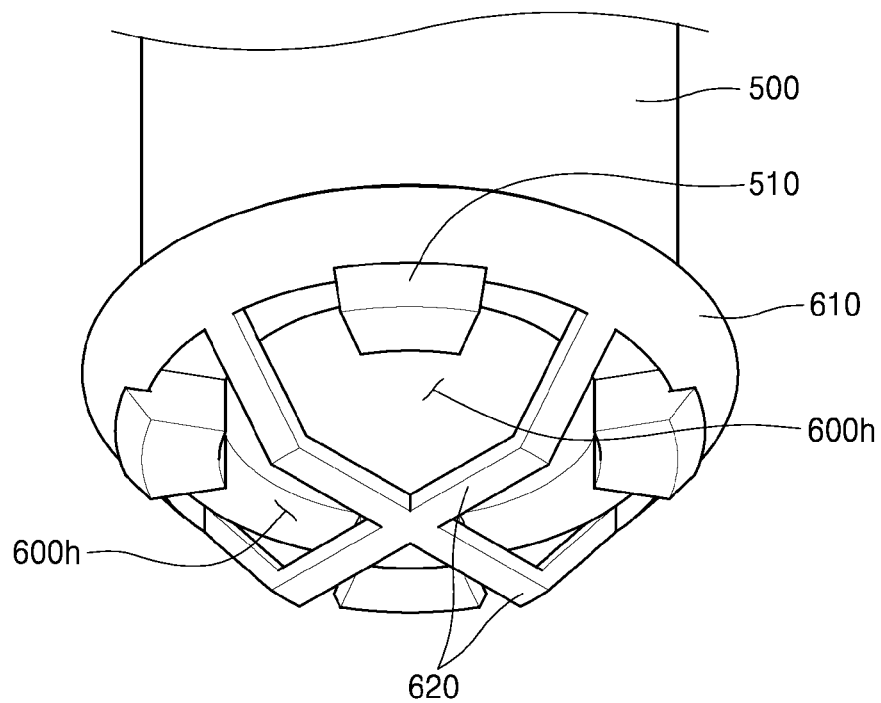

AEROSOL GENERATING DEVICE

TECHNICAL FIELD

Embodiments relate to an aerosol generating device, and more particularly, to an aerosol generating device including a structure capable of maintaining contact between a wick and a vibrator by pressing the wick toward the vibrator.

BACKGROUND ART

Recently, the demand for alternative methods to overcome the shortcomings of general cigarettes has increased. For example, there is growing demand for an aerosol generating device that generates an aerosol by heating an aerosol generating material, instead of combusting cigarettes.

DISCLOSURE OF INVENTION

Technical Problem

Recently, an aerosol generating device for generating an aerosol by atomizing an aerosol-generating material using ultrasonic vibration has been proposed. For example, an ultrasonic vibration-type aerosol generating device includes a wick which absorbs an aerosol-generating material, and a vibrator that is in contact with the wick and generates an aerosol by atomizing the aerosol-generating material absorbed in the wick through ultrasonic vibration.

However, in a conventional ultrasonic vibration-type aerosol generating device, there may be a case where the vibrator and the wick are separated by the ultrasonic vibration of the vibrator. As a result, the aerosol-generating material may not be supplied to the vibrator smoothly, and thus the atomization performance of the aerosol-generating device may be deteriorated.

The technical problems of the present disclosure are not limited to the above-described description, and other technical problems may be derived from the embodiments to be described hereinafter.

Solution to Problem

The present disclosure aims to overcome the above-described problem by providing an aerosol generating device capable of stably maintaining contact between the vibrator and the wick during the process of generating ultrasonic vibration, by pressing the wick toward the vibrator.

The aerosol generating device according to an embodiment may include a storage tank configured to store an aerosol-generating material; a wick configured to absorb the aerosol-generating material stored in the storage tank; a vibrator configured to atomize the aerosol-generating material absorbed in the wick into an aerosol by generating ultrasonic vibrations; a discharge passage configured to discharge the aerosol to an outside of the aerosol generating device; and a structure located at one end of the discharge passage and configured to press the wick toward the vibrator such that contact between the wick and the vibrator is maintained.

Advantageous Effects of Invention

The aerosol generating device according to embodiments may stably maintain contact between a vibrator and a wick while ultrasonic vibration is generated from the vibrator by pressing the wick toward the vibrator.

In addition, the aerosol generating device according to the embodiments may stably maintain contact between the vibrator and the wick so that the aerosol generating material is smoothly supplied to the vibrator, and as a result, the atomization performance may be improved.

The effects by the embodiments are not limited to the above-described effects, and effects that are not mentioned may be clearly understood by those of ordinary skill in the art from the present specification and the accompanying drawings.

BRIEF DESCRIPTION OF DRAWINGS

FIG. 1 is a block diagram of an aerosol generating device according to an embodiment.

FIG. 2 is a longitudinal cross-sectional view of an aerosol generating device according to an embodiment.

FIG. 3 is an enlarged view illustrating a partial configuration of the aerosol generating device of FIG. 2.

FIG. 4A is a side view illustrating a structure and a discharge passage of an aerosol generating device according to an embodiment.

FIG. 4B is a perspective view of the structure and the discharge passage shown in FIG. 4A.

FIG. 4C is a bottom view of the structure and the discharge passage shown in FIG. 4A.

FIG. 5A is a perspective view of a structure and a discharge passage of an aerosol generating device according to another embodiment.

FIG. 5B is a bottom view of the structure and the discharge passage shown in FIG. 5A.

FIG. 6A is a perspective view of a structure and a discharge passage of an aerosol generating device according to another embodiment.

FIG. 6B is a perspective view of a structure and a discharge passage of an aerosol generating device according to another embodiment.

FIG. 7A is a longitudinal cross-sectional view of an aerosol generating device according to another embodiment.

FIG. 7B is a perspective view showing the structure and the discharge passage of the aerosol generating device of FIG. 7A.

FIG. 8 is a longitudinal cross-sectional view of an aerosol generating device according to another embodiment.

FIG. 9A is a side view illustrating the structure and the discharge passage of the aerosol generating device shown in FIG. 8.

FIG. 9B is a perspective view of the structure and the discharge passage shown in FIG. 9A.

MODE FOR THE INVENTION

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element or layer is referred to as being "over," "above," "on," "connected to" or "coupled to" another element or layer, it can be directly over, above, on, connected or coupled to the other element or layer or intervening elements or layers may be present. In contrast, when an element is referred to as being "directly over," "directly above," "directly on," "directly connected to" or "directly coupled to" another element or layer, there are no intervening elements or layers present. Like numerals refer to like elements throughout.

In the present disclosure, "embodiments" are arbitrarily classified to facilitate description of the invention, and each of the embodiments need not be mutually exclusive. For example, configurations disclosed in one embodiment may be applied and/or implemented in other embodiments, and may be changed and applied and/or implemented within the limits not departing from the scope of the present disclosure.

In addition, in the present disclosure, the "aerosol generating device" may be a device that generates an aerosol using an aerosol-generating material. The aerosol may be directly inhaled into a user's lungs through the user's mouth.

The terms used in the present disclosure are for describing the embodiments and are not intended to limit the embodiments. In the present disclosure, a singular form also includes a plural form unless otherwise specified.

Hereinafter, the present disclosure will now be described more fully with reference to the accompanying drawings, in which exemplary embodiments of the present disclosure are shown such that one of ordinary skill in the art may easily work the present disclosure. The disclosure can, however, be embodied in many different forms and should not be construed as being limited to the embodiments set forth herein.

FIG. 1 is a block diagram of an aerosol generating device according to an embodiment.

Referring to FIG. 1, an aerosol generating device 1000 may include a processor 110, a battery 120, a sensor 130, a user interface 140, a memory 150, and an atomizer 400. In an embodiment, the atomizer 400 may include a vibrator for atomizing the aerosol generating material into an aerosol by generating ultrasonic vibrations. However, the internal structure of the aerosol generating device 1000 is not limited to the structures illustrated in FIG. 1. According to the design of the aerosol generating device 1000, it will be understood by one of ordinary skill in the art that some of the hardware components shown in FIG. 1 may be omitted or new components may be added.

In an embodiment, the aerosol generating device 1000 may consist of only a main body, in which case hardware components included in the aerosol generating device 1000 are located in the main body.

In another embodiment, the aerosol generating device 1000 may consist of a main body and a cartridge, in which case hardware components included in the aerosol generating device 1000 are located separately in the main body and the cartridge. Alternatively, at least some of hardware components included in the aerosol generating device 1000 may be located in the main body and the cartridge, respectively.

Hereinafter, an operation of each of the components will be described without being limited to location in a particular space in the aerosol generating device 1000 is located.

The processor 110 is a hardware component configured to control general operations of the aerosol generating device 1000. The processor 110 can be implemented as an array of a plurality of logic gates or can be implemented as a combination of a general purpose microprocessor and a memory in which a program executable in the microprocessor is stored. It will be understood by one of ordinary skill in the art that the processor can be implemented in other forms of hardware.

The processor 110 analyzes a result of the sensing by at least one sensor 130, and controls processes that are to be performed subsequently.

The processor 110 may control power supplied to the atomizer 400 so that the operation of the atomizer 400 is started or terminated, based on the result of the sensing by the at least one sensor 130. In addition, based on the result of the sensing by the at least one sensor 130, The processor 110 may control the amount of power supplied to the atomizer 400 and the time at which the power is supplied, so that the atomizer 400 generates appropriate amount of aerosol. For example, the processor 110 may control current or voltage supplied to the vibrator so that the vibrator of the atomizer 400 vibrates with a predetermined frequency.

In an embodiment, the processor 110 may start the operation of the atomizer 400 after receiving a user input for the aerosol generating device 1000. In addition, the processor 110 may start the operation of the atomizer 400 after detecting a puff of the user using a puff detection sensor. In addition, The processor 110 may stop supplying power to the atomizer 400 when the number of puffs reaches a preset number after counting the number of puffs by using the puff detecting sensor.

The processor 110 may control the user interface 140 based on the result of the sensing by the at least one sensor 130. For example, when the number of puffs reaches the preset number after counting the number of puffs by using the puff detecting sensor, the processor 110 may notify the user by using at least one of a light emitter, a motor or a speaker that the aerosol generating device 1000 will soon be terminated.

The battery 120 supplies electric power to be used for the aerosol generating device 1000 to operate. That is, the battery 120 may supply power so that the atomizer 400 atomizes the aerosol-generating material. In addition, the battery 120 may supply power required for operation of other hardware components included in the aerosol generating device 1000, that is, the processor 110, the sensor 130, the user interface 140, and the memory 150. The battery 120 may be a rechargeable battery or a disposable battery.

For example, the battery 120 is a nickel-based battery (for example, a nickel-metal hydride battery or a nickel-cadmium battery), or a lithium-based battery (for example, a lithium-cobalt battery, a lithium-phosphate battery, lithium titanate batteries, lithium-ion batteries, or lithium-polymer batteries). However, the type of battery 120 that may be used in the aerosol generating device 1000 is not limited by the above-described batteries. If necessary, the battery 120 may include an alkaline battery or a manganese battery.

The aerosol generating device 1000 may include at least one sensor 130. A result sensed by the at least one sensor 130 is transmitted to The processor 110, and The processor 110 may control the aerosol generating device 1000 to perform various functions such as controlling the operation of the atomizer 400, restricting smoking, determining whether a cigarette (or a cartridge) is inserted, and displaying a notification.

For example, the at least one sensor 130 may include a puff detecting sensor. The puff detecting sensor may detect a user's puff based on any one of a temperature change, a flow change, a voltage change, and a pressure change. The puff detection sensor may detect the start timing and end timing of the user's puff, and the processor 110 may determine a puff period and a non-puff period based on the detected start timing and end timing of the puff.

In addition, at least one sensor 130 may include a user input sensor. The user input sensor may be a sensor capable of receiving a user input, such as a switch, a physical button, and a touch sensor. For example, a user input sensor may be a capacitive sensor. In this case, when a user touches a predetermined region formed of a metal material, a change in capacitance occurs, and the capacitive sensor may detect a user's input by detecting the change in the capacitance. The process 110 may determine whether a user's input has occurred by comparing values before and after the change in capacitance received from the capacitive sensor. When a difference value between before and after the change in capacitance exceeds a preset threshold, the processor 110 may determine that a user's input has occurred.

In addition, at least one sensor 130 may include a motion sensor. Information about the movement of the aerosol generating device 1000 such as a tilting angle, a moving speed, and acceleration of the aerosol generating device 1000 may be obtained through the motion sensor. For example, the motion sensor may detect a state in which the aerosol generating device 1000 is moving, a state in which the aerosol generating device 1000 is stopped, a state in which the aerosol generating device 1000 is inclined at an angle within a predetermined range for a puff, and a state in which the aerosol generating device 1000 is inclined at an angle different from the range for a puff. The motion sensor may obtain motion information of the aerosol generating device 1000 using various methods known in the art. For example, the motion sensor may include an acceleration sensor capable of measuring acceleration in three directions of the x-axis, y-axis, and z-axis, and a gyro sensor capable of measuring an angular velocity in three directions.

In addition, at least one sensor 130 may include a proximity sensor. The proximity sensor refers to a sensor that detects the presence of an object or a distance of an approaching object based on an electromagnetic field or infrared light without mechanical contact, and through this, it is possible to detect whether a user approaches the aerosol generating device 1000.

In addition, at least one sensor 130 may include an image sensor. The image sensor may include, for example, a camera for obtaining an image of an object. The image sensor may recognize an object based on an image acquired by the camera. The processor 110 may analyze an image acquired through the image sensor to determine whether a user is about to use the aerosol generating device 1000. For example, when the user approaches the aerosol generating device 1000 near the lips to use the aerosol generating device 1000, the image sensor may acquire an image of the lips. The processor 110 may analyze the acquired image and determine that the user is about to use the aerosol generating device 1000 when the lips are identified from the image. Through this, the aerosol generating device 1000 may operate the atomizer 400 in advance or may preheat a heater.

In addition, the at least one sensor 130 may include a consumable detachment sensor capable of detecting the mounting or detaching of consumables (e.g., cartridges, cigarettes, etc.) that may be used in the aerosol generating device 1000. For example, the consumable detachment sensor may detect whether the consumable has been coupled to or detached from the aerosol generating device 1000 through the image sensor. In addition, the consumable detachment sensor may be an inductive sensor that detects a change in an inductance value of a coil capable of interacting with a marker of the consumable, or a capacitive sensor that detects a change in a capacitance value of a capacitor that can interact with a marker of the consumable.

In addition, at least one sensor 130 may include a temperature sensor. The temperature sensor may detect a temperature of the heater (or aerosol-generating material) of the atomizer 400. The aerosol generating device 1000 may include a separate temperature sensor for sensing the temperature of the heater. Alternatively, instead of including the separate temperature sensor, the heater may also serve as the temperature sensor. In addition, the temperature sensor may detect not only the temperature of the heater but also the temperature of internal components such as a printed circuit board (PCB) and a battery of the aerosol generating device 1000.

In addition, the at least one sensor 130 may include various sensors that measure information about the surrounding environment of the aerosol generating device 1000. For example, the at least one sensor 130 may include a temperature sensor that measures the temperature of the surrounding environment, a humidity sensor that measures the humidity of the surrounding environment, an atmospheric pressure sensor that measures the pressure of the surrounding environment, and the like.

The sensor 130 is not limited to the above-described types, and may further include various sensors. For example, the aerosol generating device 1000 may include a fingerprint sensor capable of acquiring fingerprint information from a user's finger for user authentication and security, an iris recognition sensor that analyzes an iris pattern of a pupil, a vein recognition sensor that detects the absorption of infrared rays of reduced hemoglobin in a vein from an image of a palm, and a face recognition sensor that recognizes feature points such as eyes, nose, mouth, and facial contours in a 2D or 3D method, and a radio-frequency identification (RFID) sensor.

The aerosol generating device 1000 may combine and utilize information sensed by at least one of the above-described sensors.

The user interface 140 may provide the user with information about the state of the aerosol generating device 1000. The user interface 140 may include various interfacing devices, such as a display or a light emitter for outputting visual information, a motor for outputting haptic information, a speaker for outputting sound information, input/output (I/O) interfacing devices (for example, a button or a touch screen) for receiving information input from the user or outputting information to the user, terminals for performing data communication or receiving charging power, and communication interfacing modules for performing wireless communication (for example, Wi-Fi, Wi-Fi direct, Bluetooth, near-field communication (NFC), etc.) with external devices.

However, the aerosol generating device 1000 may be implemented by selecting only some of the above-described various interfacing devices.

The memory 150 may be a hardware component configured to store various pieces of data processed in the aerosol generating device 1000, and the memory 150 may store data processed or to be processed by The processor 110. The memory 150 may include various types of memories, such as random access memory, such as dynamic random access memory (DRAM), static random access memory (SRAM), etc., read-only memory (ROM), electrically erasable programmable read-only memory (EEPROM), etc.

The memory 150 may store an operation time of the aerosol generating device 1000, the maximum number of puffs, the current number of puffs, at least one temperature profile, data on a user's smoking pattern, etc.

The atomizer 400 receives power from the battery 120 under the control of the processor 110. The atomizer 400 may receive power from the battery 120 to atomize the aerosol-generating material stored in the aerosol generating device 1000.

When the aerosol generating device 1000 includes a main body and a cartridge, the atomizer 400 may be positioned in a cartridge or positioned across the main body and the cartridge. When the atomizer 400 is located in the cartridge, the atomizer 400 may receive power from the battery 120 located in at least one of the main body and the cartridge. In addition, when the atomizer 400 is located across the main body and the cartridge, components requiring power supply in the atomizer 400 may be supplied with power from the battery 120 located in at least one of the main body and the cartridge.

The atomizer 400 generates an aerosol from an aerosol-generating material contained in the cartridge. In the present disclosure, "aerosol" refers to a suspension in which fine liquid and/or solid particles are dispersed in a gas. That is, the aerosol generated from the atomizer 400 may refer to a mixture of air and vaporized particles generated from an aerosol-generating material. For example, the atomizer 400 may convert a phase of an aerosol-generating material into a gaseous phase through vaporization and/or sublimation. In addition, the atomizer 400 may generate an aerosol by atomizing a liquid and/or solid aerosol-generating material into fine particles.

In one embodiment, the atomizer 400 may generate an aerosol from an aerosol-generating material by using an ultrasonic vibration method. The ultrasonic vibration method may mean a method of generating an aerosol by atomizing an aerosol-generating material with ultrasonic vibration generated by a vibrator.

Although not illustrated in FIG. 1, an aerosol generating system may be configured by the aerosol generating device 1000 and a separate cradle. For example, the cradle may be used to charge the battery 120 of the aerosol generating device 1000. For example, the aerosol generating device 1000 may be supplied with power from a battery of the cradle to charge the battery 120 of the aerosol generating device 1000 while being accommodated in an accommodation space of the cradle.

One embodiment may also be implemented in the form of a computer-readable recording medium including instructions executable by a computer, such as a program module executable by the computer. The computer-readable recording medium may be any available medium that can be accessed by a computer and includes both volatile and nonvolatile media, and removable and non-removable media. In addition, the computer-readable recording medium may include both a computer storage medium and a communication medium. The computer storage medium includes all of volatile and nonvolatile, and removable and non-removable media implemented by any method or technology for storage of information such as computer-readable instructions, data structures, program modules or other data. The communication medium typically includes computer-readable instructions, data structures, other data in modulated data signals such as program modules, or other transmission mechanisms, and includes any information transfer media.

FIG. 2 is a longitudinal cross-sectional view of an aerosol generating device according to an embodiment.

Referring to FIG. 2, the aerosol generating device 1000 according to an embodiment includes a housing 100, a storage tank 200, a wick 300, a vibrator 400, a discharge passage 500, and a structure 600.

At least one of the components of the aerosol generating device 1000 according to an embodiment may be the same as or similar to at least one of the components of the aerosol generating device 1000 of FIG. 1. Hereinafter, descriptions previously given will be omitted.

The housing 100 forms the overall appearance of the aerosol generating device 1000, and components of the aerosol generating device 1000 may be disposed in the inner space of the housing 100. According to embodiments, in addition to components for generating an aerosol inside the housing 100 (e.g., the storage tank 200, the wick 300, the vibrator 400, the discharge passage 500 and/or the structure 600), additional components for driving the aerosol generating device 1000 may be disposed.

In one example, a processor 110 for controlling the overall operation of the aerosol generating device 1000 and/or a battery 120 for supplying power to the components of the aerosol generating device 1000 may be disposed inside the housing 100, but components disposed inside the housing 100 are not limited thereto.

In one embodiment, the housing 100 may include a mouthpiece portion 100*m* for supplying the aerosol generated by the aerosol generating device 1000 to a user, while being in contact with a user's mouth.

The mouthpiece portion 100*m* is located at one end of the housing 100 and may be formed in a shape that can easily contact the user's mouth. For example, the mouthpiece portion 100*m* may be formed in a shape whose end gradually narrows toward the end of the housing 100 (e.g., toward the z direction in FIG. 2), but the shape of the mouthpiece portion 100*m* is not limited to the illustrated embodiment.

In one embodiment, the mouthpiece portion 100*m* may include an outlet 100*e* for supplying an aerosol to a user. For example, after passing through the discharge passage 500, the aerosol atomized by the vibrator 400 may be discharged to the outside of the aerosol generating device 1000 through the outlet 100*e*, and the user may inhale the aerosol discharged through the outlet 100*e* while the mouthpiece portion 100*m* is put in the user's mouth.

The storage tank 200 may be formed in a hollow column shape including an inner space, and an aerosol-generating material may be stored in the inner space of the storage tank 200. The aerosol-generating material stored in the inner space of the storage tank 200 may include, for example, a liquid composition.

The liquid composition may include at least one of nicotine, propylene glycol, and glycerin. The nicotine may be contained in tobacco materials obtained by shaping or reconstituting tobacco leaves. In addition, the nicotine may be natural nicotine or synthetic nicotine. For example, the nicotine may include free base nicotine, nicotine salt, or a combination thereof.

The liquid composition may contain the nicotine or a nicotine salt. The nicotine salt may be formed by adding suitable acids, including organic or inorganic acids, to nicotine. The nicotine may be a naturally generated nicotine or synthetic nicotine and may have any suitable weight concentration relative to the total solution weight of the liquid composition.

The acid for the formation of the nicotine salts may be appropriately selected in consideration of the rate of absorption of nicotine in the blood, the operating temperature of the aerosol generating device 1000, flavor or fragrance, solubility, and the like. For example, the acid for the formation of the nicotine salt may be a single acid selected from the group consisting of benzoic acid, lactic acid, salicylic acid, lauric acid, sorbic acid, levulinic acid, pyruvic acid, formic acid, acetic acid, propionic acid, butyric acid, valeric acid, caproic acid, caprylic acid, capric acid, citric acid, myristic acid, palmitic acid, stearic acid, oleic acid, linoleic acid, linolenic acid, phenylacetic acid, tartaric acid, succinic acid, fumaric acid, gluconic acid, saccharic acid, and malonic acid or malic acid, or a mixture of acids selected from the group, but it is not limited to this.

Propylene glycol and glycerin contained in the liquid composition are aerosol formers, and when the propylene glycol and the glycerin are atomized, an aerosol may be generated. For example, the liquid composition may include a glycerin and propylene glycol solution in any weight ratio to which nicotine is added.

The liquid composition may include, for example, any one component of water, solvent, ethanol, plant extract, fragrance, flavor component, and vitamin mixture, or a mixture of these components. The fragrance may include menthol, peppermint, spearmint oil, and various fruit flavoring ingredients, but is not limited thereto. Flavor elements may include ingredients that may provide a variety of flavors or savors to the user. Vitamin mixtures may be a mixture of at least one of vitamin A, vitamin B, vitamin C, and vitamin E, but are not limited thereto.

In one embodiment, the storage tank 200 may extend along the longitudinal direction of the aerosol generating device 1000 and be disposed to surround the discharge passage 500 through which the aerosol flows, but is not limited thereto. In the present disclosure, the "longitudinal direction" may mean a direction parallel to the z-axis of FIG. 2, and the corresponding expression may be used with the same meaning hereinafter.

The wick 300 may receive an aerosol-generating material from the storage tank 200. In one embodiment, at least a partial region of the wick 300 may be inserted into the inner space of the storage tank 200 to contact the aerosol-generating material stored in the storage tank 200. The aerosol-generating material stored in the inner space of the storage tank 200 may be absorbed into the wick 300 by direct contact. Accordingly, the wick 300 may receive the aerosol-generating material from the storage tank 200.

The wick 300 may include, for example, at least one of hygroscopic cotton fibers, ceramic fibers, glass fibers, and porous ceramics so as to absorb liquid or gel-type aerosol-generating materials stored in the inner space of the storage tank 200, but is not limited thereto.

The vibrator 400 may contact at least a portion of the wick 300 and may generate an aerosol by atomizing the aerosol-generating material supplied from the storage tank 200 to the wick 300.

In one embodiment, the vibrator 400 may be positioned under the wick 300 to contact at least a portion of the wick 300, and may generate a short period of vibration to atomize the aerosol-generating material absorbed in the wick 300 into an aerosol. In this case, the vibration generated by the vibrator 400 may be ultrasonic vibration, and the frequency of the ultrasonic vibration may be, for example, about 100 kHZ to about 3.5 MHz, but is not limited thereto.

The phase of the aerosol-generating material absorbed into the wick 300 is converted into a gas phase by the ultrasonic vibration generated from the vibrator 400, and thus an aerosol is generated. In other words, the vibrator 400 may generate an aerosol from an aerosol-generating material using an ultrasonic vibration method. In the present disclosure, the "ultrasonic vibration method" may mean a method of generating an aerosol by atomizing an aerosol-generating material by ultrasonic vibration, and hereinafter may be used with the same meaning.

The aerosol generated or atomized by the vibrator 400 may be discharged to the outside of the aerosol generating device 1000 through the discharge passage 500 that connects the inner space of the housing 100 with the outside of the aerosol generating device 1000. The user may inhale the aerosol discharged to the outside of the aerosol generating device 1000 through the discharge passage 500.

In one embodiment, the vibrator 400 may be fixed to the inner space of the housing 100 through a support member 410. In addition, at least one region of the outer circumferential surface of the vibrator 400 may be wrapped by a sealing member 420 that prevents the aerosol-generating material leaking into other components of the aerosol generating device 1000. As a result, failure or malfunction of the aerosol generating device 1000 may be prevented.

In one embodiment, the discharge passage 500 may extend along the longitudinal direction of the aerosol generating device 1000 to connect the inner space of the housing 100 with the outside of the aerosol generating device 1000, but the shape of the discharge passage 500 is not limited thereto.

The structure 600 may be disposed in the discharge passage 500 to contact at least one region of the wick 300, and may continuously maintain contact between the wick 300 and the vibrator 400 by applying pressure (i.e., −z direction in FIG. 2) on the vibrator 400 toward the wick 300 (i.e., −z direction in FIG. 2).

In the case of an aerosol generating device without a structure for pressing the wick 300 toward the vibrator 400, the wick 300 may be separated from the vibrator 400 due to the ultrasonic vibration generated in the vibrator 400. If the wick 300 is separated from the vibrator 400, the supply of the aerosol-generating material to the vibrator 400 may not be smoothly performed, and as a result, the aerosol generation efficiency (i.e., atomization performance) of the aerosol generating device may be lowered.

In this respect, the aerosol generating device 1000 according to an embodiment may maintain continuous contact between the wick 300 and the vibrator 400 by using the structure 600 capable of pressing the wick 300 toward the vibrator 400. Accordingly, the aerosol generating device 1000 may smoothly supply the aerosol-generating material to the vibrator 400 even while vibration is generated in the vibrator 400, thereby preventing a decrease in the efficiency of generating aerosols by vibration.

In one embodiment, the structure 600 may be coupled to one region (i.e., an end portion) of the discharge passage 500 adjacent to the wick 300 to press the wick 300 in a direction toward the vibrator 400. For example, the structure 600 may be coupled to a region of the discharge passage 500 by various coupling method, such as screwing, interference fit, etc. As another example, the structure 600 may be supported by a protruding member formed in the discharge passage 500, but embodiments are not limited thereto.

As shown in FIG. 2, the structure 600 may be formed in a curved shape such that the curved portion contacts the wick 300, pressing the wick 300 toward the vibrator 400. For example, the structure 600 may be formed in a convex shape curved toward the wick 300, but the shape of the structure 600 is not limited thereto.

In one embodiment, the structure 600 may include a flexible material, so that the vibration generated in the vibrator 400 may not be affected by the structure 600 pressing the wick 300 toward the vibrator 400. The structure 600 may include, for example, at least one of rubber, plastic, and metal having elastic properties, but is not limited thereto.

If the structure 600 is formed of a non-elastic material, the vibration generated by the vibrator 400 may be attenuated or the waveform of the vibration may be deformed because of the structure 600 pressing the wick 300 toward the vibrator 400, which may cause deterioration of atomization performance of the aerosol generating device 1000.

In this respect, the aerosol generating device 1000 according to an embodiment may not attenuate the vibration generated by the vibrator 400 and may not change the waveform of the vibration because the structure 600 pressing the wick 300 toward the vibrator 400 has elasticity.

Hereinafter, a process in which the wick 300 is pressed toward the vibrator 400 by the structure 600 will be described in detail with reference to FIG. 3.

FIG. 3 is an enlarged view illustrating a partial configuration of the aerosol generating device of FIG. 2 FIG. 3 shows an enlarged view of the wick 300 and the structure 600 illustrated in FIG. 2, and descriptions previously given will be omitted hereinafter.

Referring to FIG. 3, the structure 600 may be disposed in the discharge passage 500 to contact at least one region of the wick 300, pressing the wick 300 toward the vibrator 400.

In one embodiment, the structure 600 may be coupled to one end of the discharge passage 500 which is adjacent to the wick 300, and at least one region of the structure 600 may be curved toward the wick 300. For example, as shown in FIG. 3, the structure 600 may be formed in a convex shape curved toward the wick 300 when viewed from the side. The curvature of the curved region of the structure 600 may vary according to embodiments.

The curved region of the structure 600 may contact at least one region of the wick 300, such that the wick 300 is pressed toward the vibrator 400 by the contact between the wick 300 and the structure 600.

As the wick 300 is pressed toward the vibrator 400 by the structure 600, the distance between the vibrator 400 and the structure 600 may decrease. The relationship between the distance between the vibrator 400 and the structure 600 in the state where the wick 300 is compressed by the structure 600 and the thickness of the wick 300 in an uncompressed state may be expressed as Equation 1 below.

$$b \geq a \qquad \text{[Equation 1]}$$

In Equation 1, 'a' refers to the distance between the vibrator 400 and the structure 600 when the wick 300 is pressed by the structure 600, and 'b' refers to the thickness of the wick 300 in a state of not being pressed by the structure 600.

In the present disclosure, "the distance between the vibrator and the structure" refers to the shortest distance between the vibrator 400 and the structure 600, and the expression may be used with the same meaning in the following.

In addition, the wick 300 may be divided into a first portion 300a in contact with the vibrator 400 and a second portion 300b connecting the first portion 300a to the inner space of the storage tank 200. In the present disclosure, "the thickness of the wick" refers to the thickness of the first portion 300a, and the expression may be used with the same meaning in the following.

As shown in Equation 1, as the wick 300 is compressed toward the vibrator 400 by the structure 600, the distance between the vibrator 400 and the structure 600 may decrease. Therefore, the distance a between the vibrator 400 and the structure 600 may be less than or equal to the thickness b of the wick 300 in an uncompressed state.

Preferably, as shown in Equation 2 below, the distance a between the vibrator 400 and the structure 600 may be less than or equal to the thickness b of the wick 300 in an uncompressed state and greater than or equal to b/2.

$$b \geq a \geq \frac{b}{2} \qquad \text{[Equation 2]}$$

When a pressure equal to or greater than a certain value is applied to the wick 300, the pressure applied from the structure 600 to the wick 300 is transmitted to the vibrator 400 and the vibration generated in the vibrator 400 may be attenuated or the waveform of the vibration may be deformed. As a result, the atomization performance of the aerosol generating device 1000 may be deteriorated. For example, if the vibrator 400 normally generates a vibration of about 2.7 MHz, when a pressure is applied to the wick 300, the vibration frequency attenuated to about 2.5 MHz, which may deteriorate the atomization performance of the aerosol generating device 1000.

In the present disclosure, a 'designated value' may mean a pressure value at which the vibration generated in the vibrator 400 is attenuated or the waveform of the vibration starts to be deformed by the pressure applied to the wick 300 in the structure 600. The designated value may be derived through an experiment, and the designated value may be modified depending on the shape and/or material of the structure 600.

As the pressure equal to or greater than the designated value is applied to the wick 300, the distance a between the vibrator 400 and the structure 600 may become less than b/2. In this case, attenuation of vibration generated in the vibrator 400 or deformation of a waveform may occur, thereby deteriorating atomization performance.

In this respect, according to an embodiment, the structure 600 presses the wick 300 to the extent that the distance a between the structure 600 and the vibrator 400 does not decrease below b/2. Accordingly, the aerosol generating device 1000 according to an embodiment may not deform the vibration generated from the vibrator 400 while continuously maintaining contact between the wick 300 and the vibrator 400.

FIG. 4A is a side view illustrating a structure for pressing the wick and a discharge passage of an aerosol generating device according to an embodiment, FIG. 4B is a perspective view of the structure and the discharge passage shown in FIG. 4A, and FIG. 4C is a bottom view of the structure and the discharge passage shown in FIG. 4A.

FIG. 5A is a perspective view of a structure for pressing the wick and a discharge passage of an aerosol generating device according to another embodiment, and FIG. 5B is a bottom view of the structure and the discharge passage shown in FIG. 5A.

A discharge passage 500 and a structure 600 shown in FIGS. 4A to 4C and/or FIGS. 5A to 5B may be an example of the discharge passage 500 and the structure 600 applied to the aerosol generating device 1000 shown in FIGS. 2 and 3, and descriptions previously given will be omitted hereinafter.

Referring to FIGS. 4A to 4C and FIGS. 5A to 5B, the structure 600 according to an embodiment may include a flange 610, at least one pressing portion 620, and at least one hole 600h.

The flange 610 may be disposed to surround a region of the discharge passage 500 adjacent to the wick 300. Depending on the embodiment, the discharge passage 500 may be formed in various shapes, and the flange 610 of the structure 600 may also be formed in various shapes depending on the shape of the discharge passage 500.

Referring to FIGS. 4A to 4C, for example, the discharge passage 500 may be formed in a hollow cylindrical shape, and the flange 610 may be disposed to surround the outer circumferential surface of the cylindrical discharge passage 500. In other words, the flange 610 is formed in a donut shape when viewed from the bottom, and may be disposed to surround the outer circumferential surface of the discharge passage 500.

Referring to FIGS. 5A to 5B, as another example, the discharge passage 500 may be formed in a hollow rectangular column shape, and the flange 610 may be disposed to surround the outer circumferential surface of the discharge passage 500 having a rectangular column shape. That is, the flange 610 may be formed in a rectangular strip shape when viewed from the bottom, and may be disposed to surround the outer circumferential surface of the discharge passage 500.

However, the shapes of the discharge passage 500 and the flange 610 are not limited to the above-described embodiments, and in other embodiments, the discharge passage 500 and the flange 610 may be formed in different shapes.

In one embodiment, the flange 610 may reduce the gap between the discharge passage 500 and the structure 600 and firmly fix the structure 600 to the discharge passage 500, by surface contact with the outer circumferential surface of the discharge passage 500.

For example, when the discharge passage 500 and the flange 610 are in point contact and/or line contact, a gap may be present between the discharge passage 500 and the flange 610 so that the structure 600 may not be firmly fixed to the discharge passage 500. As a result, while the aerosol generating device 1000 is in use, the structure 600 may be separated from the discharge passage 500 and thus the wick 300 may not be pressed toward the vibrator (for example, vibrator 400 of FIGS. 2 and 3).

On the other hand, the aerosol generating device according to an embodiment (for example, the aerosol generating device 1000 of FIGS. 2 and 3) may minimize the space between the discharge passage 500 and the structure 600 by surface contact between the flange 610 and the discharge passage 500, thereby minimizing the mounting space or arrangement space of the structure 600 in the aerosol generating device. Accordingly, the design convenience of the aerosol generating device is improved, and the aerosol generating device may be downsized.

In addition, since the structure 600 is firmly fixed to the discharge passage 500 by surface contact between the flange 610 and the discharge passage 500, it is possible to prevent the structure 600 from being separated from the discharge passage 500 during use of the aerosol generating device.

The at least one pressing portion 620 may be formed in a curved shape, and may press the wick 300 in a specific direction by contacting one region of the wick 300.

For example, at least one pressing portion 620 may be formed in a convex shape curved toward the wick 300, and may press the wick 300 in a direction toward the vibrator (e.g., in the −z direction in FIG. 2).

In one embodiment, the at least one pressing portion 620 may extend from one point of the flange 610 to another point of the flange 610 and may be formed in a shape having a specified curvature when viewed from the side. For example, when viewed from the side, the at least one pressing portion 620 may be formed in a "U" shape. In this case, the convex portion of the at least one pressing portion 620 may come in contact with one surface of the wick 300 facing the discharge passage 500, so that the wick 300 may be pressed toward the vibrator.

Although not shown in the drawings, in another embodiment, at least one pressing portion 620 may be formed to extend toward the wick 300 from one point of the flange 610 in a curved shape. In other words, at least one pressing portion 620 according to another embodiment may not extend from one point of the flange 610 to another point, but may be formed to protrude in a curved shape from the flange 610 toward the wick 300.

In FIGS. 4A-4C, the different pressing portions 620 are arranged to cross at right angles, but embodiments are not limited thereto. Depending on the embodiment, different pressing portions 620 may be disposed in parallel or may be disposed to cross at a different angle.

In addition, FIGS. 4A-5B illustrate that the structure 600 includes two pressing portions 620, the number of the pressing portions 620 is not limited thereto. For example, the structure 600 may include only one pressing portion 620 or three or more pressing portions 620.

The at least one hole 600h may be formed through at least one region of the structure 600, and may serve as a passage for the aerosol flowing into the discharge passage 500.

In one embodiment, at least one hole 600h may be disposed between the flange 610 and the at least one pressing portion 620, and elastic properties of the at least one pressing portion 620 may be improved by the above-described arrangement of the at least one hole 600h. Accordingly, the at least one pressing portion 620 may minimize attenuation of the vibration generated by the vibrator or the deformation of the waveform, while maintaining the contact between the wick 300 and the vibrator.

The shape and/or number of the at least one hole 600h is not limited to the embodiments shown in the drawings, and depending on the embodiment, the shape and/or number of at least one hole 600h may be changed.

In one embodiment, the structure 600 may be coupled to a region of the discharge passage 500 adjacent to the wick 300.

For example, the discharge passage 500 may include a protruding member 510 protruding in a radial direction from the outer circumferential surface of the discharge passage 500, and the protruding member 510 may is inserted into at least one hole 600h to support at least one region of the structure 600, so that the discharge passage 500 and the structure 600 may be coupled. The protruding member 510 may support a region of the flange 610 that is in surface contact with the discharge passage 500 while being inserted into the at least one hole 600*h*, but is not limited thereto.

In another embodiment, the discharge passage 500 may further include a fixing member 520 for restricting movement of the structure 600 in a specific direction. For example, as shown in FIG. 4A, the fixing member 520 may be radially disposed along the outer circumferential surface of the discharge passage 500 to prevent the structure 600 from moving upward, but embodiments are not limited thereto.

Although the movement of the structure 600 toward the wick 300 may be restricted by the protruding member 510, the structure 600 may move in another direction due to the vibration generated from the vibrator. For example, if the structure 600 moves away from the wick 300 (i.e., if the structure 600 moves upward), a separation between the structure 600 and the wick 300 may occur and the wick 300 may not be pressed toward the vibrator.

In this respect, the aerosol generating device according to an embodiment may limit the movement of the structure 600 in the opposite direction of the wick 300 by the fixing member 520 formed in the discharge passage 500. That is, since the structure 600 may be firmly fixed to the discharge passage 500 by the fixing member 520, the structure 600 may be prevented from being separated from the wick 300 during use of the aerosol generating device.

Although not shown in the drawings, in another embodiment, the structure 600 may be fixed to the discharge passage 500 by being screwed or by being forcefully fitted to the discharge passage 500. For example, for screwing the structure 600 and the discharge passage 500, a circular screw surface may be formed at a portion where the structure 600 and the discharge passage 500 are coupled to each other.

FIG. 6A is a perspective view of a structure and a discharge passage of an aerosol generating device according to another embodiment, and FIG. 6B is a perspective view of a structure and a discharge passage of an aerosol generating device according to another embodiment.

Referring to FIGS. 6A and 6B, a structure 600 of the aerosol generating device is coupled to a region of a discharge passage 500, and may include at least one hole 600*h*, a flange 610, at least one pressing portion 620 and a contact portion 630.

When compared with the embodiments of FIGS. 4A-5B, the structure 600 of FIG. 6A and FIG. 6B may further include the contact portion 630. Therefore, descriptions of other components which were previously given will be omitted hereinafter.

The contact portion 630 of the structure 600 may be positioned in one region of the at least one pressing portion 620 to contact one surface of the wick 300 facing the discharge passage 500. For example, the contact portion 630 may contact one region of the wick 300 and press the wick 300 toward a vibrator (e.g., the vibrator 400 of FIGS. 2 and 3).

In one embodiment, the contact portion 630 may be disposed to make surface contact with the wick 300, and the structure 600 may press the wick 300 more effectively by the surface contact between the contact portion 630 and the wick 300.

Referring to FIG. 6A, the contact portion 630 may be disposed at the intersection of the at least one pressing portion 620. However, the arrangement position of the contact portion 630 is not limited to the above-described embodiment.

Referring to FIG. 6B, the contact portion 630 may be arranged to connect one point of one pressing portion 620 to one point of another pressing portion 620, such that the contact portion 630 may press the wick 300 toward the vibrator.

In addition, depending on the embodiment, the contact portion 630 may be formed in a circular shape as shown in FIG. 6A or may be formed in a polygonal (e.g., quadrangle) shape as shown in FIG. 6B, but the shape of the contact portion 630 is not limited to the illustrated embodiments.

In an embodiment, the contact portion 630 may include at least one through hole 631 penetrating one region of the contact portion 630. The at least one through hole 631 may operate as a passage through which the aerosol atomized by the vibrator moves toward the discharge passage 500.

For example, the aerosol atomized by the vibrator passes may move or flow into the discharge passage 500 through at least one hole 600*h* and/or at least one through hole 631. Through the discharge passage 500, the aerosol may be discharged to the outside of the aerosol generating device and supplied to the user.

FIG. 7A is a longitudinal cross-sectional view of an aerosol generating device according to another embodiment, and FIG. 7B is a perspective view showing the structure and the discharge passage of the aerosol generating device of FIG. 7A. FIG. 7B is an enlarged view of region A of the aerosol generating device 1000 in FIG. 7A.

Referring to FIGS. 7A and 7B, an aerosol generating device 1000 may include a housing 100, a processor 110, a battery 120, a storage tank 200, a wick 300, and a vibrator 400, a discharge passage 500, a structure 600, and a medium 700.

When compared with FIGS. 2 and 4B, the aerosol generating device 1000 of FIGS. 7A and 7B may further include the protruding portion 640 and the medium 700. Therefore, descriptions of other components which were previously given will be omitted hereinafter.

In the discharge passage 500 connecting the inner space of the housing 100 with the outside of the aerosol generating device 1000, a medium 700 may be arranged to supply or add flavor to the aerosol passing through the discharge passage 500.

The medium 700 may include ingredients capable of providing various flavors and/or fragrances to a user. In one example, the medium 700 may be in a solid state, and may be provided in the form of small-sized particles such as powder or granules, so that the aerosol passes through the medium. In another example, the medium 700 may include a tobacco-containing material including a volatile tobacco flavor component, or may include an additive material (e.g., a flavoring agent, a wetting agent, or an organic acid), a fragrant material (e.g., menthol), a moisturizing agent, a plant extract, a flavor, a vitamin mixture, or various combinations of these components.

As the aerosol passes through the medium 700 in the discharge passage 500 before being discharged to the outside, flavor and/or fragrance may be added to the aerosol, and as a result, the user may inhale the aerosol supplied with flavor and/or fragrance.

In one embodiment, the structure 600 may further include a protruding portion 640 for generating a vortex in at least one hole 600*h*. For example, the protruding portion 640 may be formed to protrude in a direction from the at least one pressing portion 620 toward the at least one hole 600*h*.

The position and shape of the protruding portion 640 shown in FIG. 7B is only an example, and the position and/or shape of the protruding portion 640 is not limited to the illustrated embodiment.

The aerosol atomized by the vibrator 400 may contact the protruding portion 640 while passing through the at least one hole 600h toward the discharge passage 500, and as a result, a vortex may be generated inside the discharge passage 500 and/or at least one hole 600*h*.

The aerosol passing through the at least one hole 600*h* and the discharge passage 500 by the vortex generated inside the discharge passage 500 and/or the at least one hole 600*h* may be evenly diffused throughout the discharge passage 500.

As the aerosol spreads evenly throughout the discharge passage 500, the contact area, contact time, and/or the number of contact points between the aerosol passing through the discharge passage 500 and the medium 700 may increase, and as a result, the flavor and/or fragrance of the aerosol passing through the medium 700 may be improved. Accordingly, a user's smoking feeling may be improved by the protruding portion 640 and the medium 700 of the structure 600.

FIG. 8 is a longitudinal cross-sectional view of an aerosol generating device according to another embodiment, FIG. 9A is a side view illustrating the structure and the discharge passage of the aerosol generating device shown in FIG. 8, and FIG. 9B is a perspective view of the structure and the discharge passage shown in FIG. 9A.

Referring to FIGS. 8, 9A and 9B, an aerosol generating device 1000 according to another embodiment may include a housing 100, a processor 110, a battery 120, a storage tank 200, a wick 300, a vibrator 400, a discharge passage 500, and a structure 600. When compared with other embodiments described above, the aerosol generating device 1000 of FIG. 8 may the structure 600 has a different shape. Therefore, descriptions of other components which were previously given will be omitted hereinafter.

The structure 600 may be disposed at one end of the discharge passage 500 adjacent to the wick 300, and region may be formed in a bent shape. In one embodiment, at least one pressing portion 620 includes a first portion that extends toward the wick 300, and a second portion that is bent angularly with respect to the first portion and contacts the wick 300.

As such, the bent region (i.e., second portion) of the structure 600 may make surface contact with the wick 300 and press the wick 300 toward the vibrator 400 (for example, in the −z direction in FIG. 2). As a result, the contact between the wick 300 and the vibrator 400 may be stably maintained.

In one example, the structure 600 may be made of an elastic material. Accordingly, while pressing the wick 300 toward the vibrator 400, the structure 600 may not reduce the vibration generated by the vibrator 400.

Examples of a material for the structure 600 may include, but are not limited to, rubber, plastic, and metal having elastic properties. As a result, attenuation or modification of vibration generated by the vibrator 400 due to the structure 600 may be prevented.

According to an embodiment, the structure 600 may include a flange 610, at least one pressing portion 620, and at least one hole 600*h*, and may be coupled to at least one region of the discharge passage 500.

The flange 610 is disposed so as to surround one region of the discharge passage 500 adjacent to the wick 300, and thus may make surface contact with the discharge passage 500. The shape of the flange 610 may correspond to the shape of the discharge passage 500. That is, depending on the embodiment, the flange 610 may be disposed to surround the outer circumferential surface of the cylindrical discharge passage 500, or may be disposed to surround the outer circumferential surface of the polygonal column-shaped discharge passage 500. The shape of the discharge passage 500 and/or the flange 610 is not limited to the above-described embodiment.

In one embodiment, the flange 610 may reduce the distance between the discharge passage 500 and the structure 600. To this end, the flange may be firmly fixed to the discharge passage 500 by making surface contact with the outer circumferential surface of the discharge passage 500.

If the discharge passage 500 and the flange 610 are in point contact and/or line contact, a gap may be present between the discharge passage 500 and the flange 610, and the structure 600 may not be firmly fixed to the discharge passage 500. As a result, while the aerosol generating device 1000 is in use, the structure 600 may be separated from the discharge passage 500 and thus the wick 300 may not be pressed toward the vibrator 400.

On the other hand, the aerosol generating device according to an embodiment may reduce the space between the discharge passage 500 and the structure 600 by the flange 610 in surface contact with the discharge passage 500. As a result, it is possible to minimize the mounting space or arrangement space of the structure 600 inside the aerosol generating device.

In addition, since the structure 600 is firmly fixed to the discharge passage 500 by the flange 610, it is possible to prevent the structure 600 from being separated from the discharge passage 500 during use of the aerosol generating device.

At least one pressing portion 620 may have a portion which is bent angularly such that the bent portion makes surface contact with the wick 300 and presses the wick 300 toward the vibrator 400.

For example, the at least one pressing portion 620 may extend from one point of the flange 610 to another point of the flange 610, but is not limited thereto. As another example, the at least one pressing portion 620 may not extend from one point of the flange 610 to another point, but may be formed to protrude toward the wick 300. In this case, the at least one pressing portion 620 may have a curved shape.

FIGS. 9A and 9B illustrate that the different pressing portions 620 cross at right angles, but the arrangement structure of the pressing portion 620 is not limited to the embodiment shown in the drawings. Depending on the embodiment, different pressing portions 620 may be disposed in parallel or may be disposed to cross at a predetermined angle.

In addition, although the structure 600 shown in FIGS. 9A and 9B includes two pressing portions 620 crossing each other, the number of the pressing portions are not limited thereto. Depending on the embodiment, the structure 600 may include only one pressing portion 620 or may include three or more pressing portions 620.

The at least one hole 600*h* is formed through at least one region of the structure 600, and may serve as a passage for the aerosol to move to the discharge passage 500.

In one embodiment, the at least one hole 600*h* may be disposed between the flange 610 and the at least one pressing portion 620, and elastic properties of the at least one pressing portion 620 may be improved by the above-described arrangement of the at least one hole 600*h*. Accordingly, the at least one pressing portion 620 may minimize attenuation or modification of the vibration generated by the vibrator while maintaining the contact between the wick 300 and the vibrator.

The shape and/or number of the at least one hole 600*h* is not limited to the embodiment shown in the drawings, and depending on the embodiment, the shape and/or number of at least one hole 600*h* may be changed.

As aforementioned, the structure 600 may further include a contact portion (e.g., a contact portion 630 of FIGS. 6A and 6B) located in one region of the at least one pressing portion 620 and in surface contact with the one region of the wick 300.

The aerosol generating device 1000 may more effectively maintain the contact between the wick 300 and the vibrator 400 through the above-described contact portion of the structure 600. Accordingly, the aerosol-generating material may be smoothly supplied to the vibrator 400, and the atomization performance of the aerosol-generating device 1000 may be improved.

That is, the aerosol generating device 1000 according to the above-described embodiments may stably maintain contact between the wick 300 and the vibrator 400 during the process of generating vibration from the vibrator 400 by using the structure 600 for pressing the wick 300 toward the vibrator 400.

As a result, deterioration of atomization performance due to the separation of the wick 300 from the vibrator 400 may be prevented.

In addition, the structure 600 is firmly fixed to the discharge passage 500 by surface contact, and the arrangement space or mounting space of the structure 600 may be minimized, thereby downsizing the aerosol generating device 1000 and improving design freedom thereof.

The descriptions of the above-described embodiments are merely examples, and it will be understood by one of ordinary skill in the art that various changes and equivalents thereof may be made. The disclosed methods should be considered in a descriptive sense only and not for purposes of limitation. The scope of the disclosure should be defined by the appended claims, and all differences within the scope equivalent to those described in the claims will be construed as being included in the scope of protection defined by the claims.

The invention claimed is:

1. An aerosol generating device comprising:
   a storage tank configured to store an aerosol-generating material;
   a wick configured to absorb the aerosol-generating material stored in the storage tank;
   a vibrator configured to atomize the aerosol-generating material absorbed in the wick into an aerosol by generating ultrasonic vibrations;
   a discharge passage configured to discharge the aerosol to an outside of the aerosol generating device; and
   a structure located at one end of the discharge passage and configured to press the wick toward the vibrator such that contact between the wick and the vibrator is maintained,
   wherein the structure includes:
   a flange arranged to surround the one end of the discharge passage;
   at least one pressing portion extending from the flange toward the wick such that the at least one pressing portion presses the wick toward the vibrator; and
   at least one hole formed in the structure by arrangement of the at least one pressing portion and the flange such that the aerosol flows into the discharge passage through the at least one hole,
   wherein the discharge passage includes at least one protruding member protruding from an outer surface of the discharge passage and supporting the structure by being inserted into the at least one hole and contacting the structure.

2. The aerosol generating device of claim 1, wherein the structure includes a flexible material.

3. The aerosol generating device of claim 2, wherein the structure is coupled to an end of the discharge passage which is adjacent to the wick.

4. The aerosol generating device of claim 1, wherein a distance between the structure and the vibrator when the wick is pressed by the structure is less than or equal to a thickness of the wick when not pressed by the structure.

5. The aerosol generating device of claim 4, wherein the distance between the structure and the when the wick is pressed by the structure is greater than or equal to half the thickness of the wick when not pressed by the structure.

6. The aerosol generating device of claim 1, wherein the flange is in surface contact with the discharge passage.

7. The aerosol generating device of claim 1, wherein the at least one pressing portion extends from one point of the flange to another point of the flange and has a portion curved toward the wick.

8. The aerosol generating device of claim 7, wherein the structure further includes a contact portion located in the at least one pressing portion and configured to make surface contact with the wick.

9. The aerosol generating device of claim 8, wherein the contact portion includes at least one through hole configured to pass the aerosol flowing to the discharge passage.

10. The aerosol generating device of claim 1, wherein the discharge passage further includes a fixing member configured to prevent the structure from moving in a direction away from the wick.

11. The aerosol generating device of claim 1, further comprising a medium arranged in the discharge passage and configured to add flavor to the aerosol passing through the discharge passage,
   wherein the structure further includes a protruding portion protruding from the at least one pressing portion toward the at least one hole, and configured to generate a vortex as the aerosol passing through the at least one hole contacts the protruding portion.

12. The aerosol generating device of claim 1, wherein the structure includes a first portion that extends toward the wick and a second portion that is angularly bent with respect the first portion such that the second portion contacts the wick.

* * * * *